(12) United States Patent
Piantoni et al.

(10) Patent No.: US 10,384,376 B2
(45) Date of Patent: Aug. 20, 2019

(54) UNIT AND METHOD FOR FORMING ABSORBENT PADS OF ABSORBENT ARTICLES

(71) Applicant: GDM S.p.A., Bologna (IT)

(72) Inventors: Matteo Piantoni, Albino (IT); Valerio Soli, Bologna (IT)

(73) Assignee: GDM S.p.A., Bologna (IT)

( * ) Notice: Subject to any disclaimer, the term of this patent is extended or adjusted under 35 U.S.C. 154(b) by 166 days.

(21) Appl. No.: 15/312,281

(22) PCT Filed: May 13, 2015

(86) PCT No.: PCT/IB2015/053516
§ 371 (c)(1),
(2) Date: Nov. 18, 2016

(87) PCT Pub. No.: WO2015/177687
PCT Pub. Date: Nov. 26, 2015

(65) Prior Publication Data
US 2017/0080610 A1    Mar. 23, 2017

(30) Foreign Application Priority Data

May 23, 2014    (IT) .............................. BO2014A0305

(51) Int. Cl.
*B29C 41/36*      (2006.01)
*A61F 13/15*      (2006.01)
(Continued)

(52) U.S. Cl.
CPC ........ *B29C 41/36* (2013.01); *A61F 13/15626* (2013.01); *A61F 13/15658* (2013.01);
(Continued)

(58) Field of Classification Search
CPC ......... B29C 41/36; B29C 41/38; B29C 41/02; A61F 13/15804; A61F 13/15626; A61F 13/15658
See application file for complete search history.

(56) References Cited

U.S. PATENT DOCUMENTS 5,028,224 A  *  7/1991  Pieper ............... A61F 13/15577
                                                    19/304
5,044,052 A     9/1991  Hertel et al.
(Continued)

FOREIGN PATENT DOCUMENTS

CN        101257874 A     9/2008
CN        102348441 A     2/2012
(Continued)

OTHER PUBLICATIONS

International Search Report and Written Opinion dated Sep. 11, 2015 for counterpart PCT Application No. PCT/IB2015/053516.
(Continued)

*Primary Examiner* — Joseph S Del Sole
*Assistant Examiner* — Mohamed K Ahmed Ali
(74) *Attorney, Agent, or Firm* — Shuttleworth & Ingersoll, PLC; Timothy Klima

(57) ABSTRACT

A unit for making absorbent pads of absorbent articles including a drum for forming the absorbent pads and a hood for feeding a first and a second absorbent material to at least part of the peripheral surface of the drum; the hood has a chamber for mixing the first and the second absorbent materials and an opening for dispensing the first and the second absorbent materials facing at least part of the peripheral surface of the drum; the unit includes at least a first and a second duct for feeding the second absorbent material into the hood and means for distributing the second absorbent material both of the first feed duct and of the second feed duct; the first and the second ducts are connected to the same distribution means.

13 Claims, 2 Drawing Sheets

(51) Int. Cl.
   *B29C 41/02*    (2006.01)
   *B29C 41/38*    (2006.01)
   *B29L 31/48*    (2006.01)

(52) U.S. Cl.
   CPC ........ *A61F 13/15804* (2013.01); *B29C 41/02* (2013.01); *B29C 41/38* (2013.01); *B29K 2995/0068* (2013.01); *B29L 2031/4878* (2013.01)

(56) References Cited

U.S. PATENT DOCUMENTS

| | | | |
|---|---|---|---|
| 6,033,199 A * | 3/2000 | Vonderhaar | A61F 13/15658 118/301 |
| 2009/0321986 A1 | 12/2009 | Perego et al. | |
| 2011/0297080 A1 | 12/2011 | Pastrello et al. | |
| 2013/0062802 A1 | 3/2013 | Goda et al. | |
| 2014/0027943 A1 | 1/2014 | Hoshika | |

FOREIGN PATENT DOCUMENTS

| | | |
|---|---|---|
| CN | 102892394 A | 1/2013 |
| CN | 103347472 A | 10/2013 |
| EP | 2554144 | 2/2013 |
| GB | 2191515 | 12/1987 |
| JP | 2009112347 A | 5/2009 |

OTHER PUBLICATIONS

Chinese Office Action dated Nov. 2, 2018 for counterpart Chinese Patent Application No. 201580026712.3.

* cited by examiner

UNIT AND METHOD FOR FORMING ABSORBENT PADS OF ABSORBENT ARTICLES

This application is the National Phase of International Application PCT/IB2015/053516 filed May 13, 2015 which designated the U.S. and that International Application was published under PCT Article 21(2) in English.

This application claims priority to Italian Patent Application No. BO2014A000305 filed May 23, 2014, which application is incorporated by reference herein.

TECHNICAL FIELD

This invention relates to a unit and method for forming absorbent pads of absorbent articles.

The term "absorbent pad" is used to denote the part of the absorbent article designed for absorbing and retaining liquids.

BACKGROUND ART

Usually, the absorbent pads comprise an absorbent matrix made from natural fibre particles (known as "fluff") blended with particles of absorbent polymer material ("SAP").

In order to increase the absorption capacity, absorbent pads have been developed which are equipped with one or more discrete layers of particles of absorbent polymer material ("SAP"), positioned on the absorbent matrix.

There are prior art units for making absorbent pads which comprise a drum for forming the absorbent pads and a hood for feeding natural fibre particles and particles of absorbent polymer material. More specifically, the hood has a chamber for mixing natural fibre particles and particles of absorbent polymer material designed to define the absorbent matrix and a dispensing opening facing at least part of the peripheral surface of the drum.

With regard to the feeding of the particles of absorbent polymer material ("SAP") of the mixing chamber, the unit comprises a first feed duct which leads into the mixing chamber.

In order to make the one or more discrete layers of particles of absorbent polymer material ("SAP"), the unit comprises a second duct for feeding the particles of absorbent material ("SAP") which leads close to the dispensing opening.

Generally, the second feed duct feeds the particles of absorbent material intermittently to make the discrete layers of particles of absorbent polymer material.

The particles of absorbent material which are not dispensed from the second feed duct are introduced again into the distribution plant of the second feed duct until they are subsequently dispensed from the second duct.

However, it has been found that the recirculation operation deteriorates the absorbent, adversely affecting the capacity for absorption and drainage of liquids.

AIM OF THE INVENTION

The aim of this invention is to overcome the above-mentioned drawbacks of the prior art.

BRIEF DESCRIPTION OF THE DRAWINGS

The invention will now be described with reference to the accompanying drawings which illustrate a non-limiting embodiment of it and in which.

DETAILED DESCRIPTION OF PREFERRED EMBODIMENTS OF THE INVENTION

Figure 1:
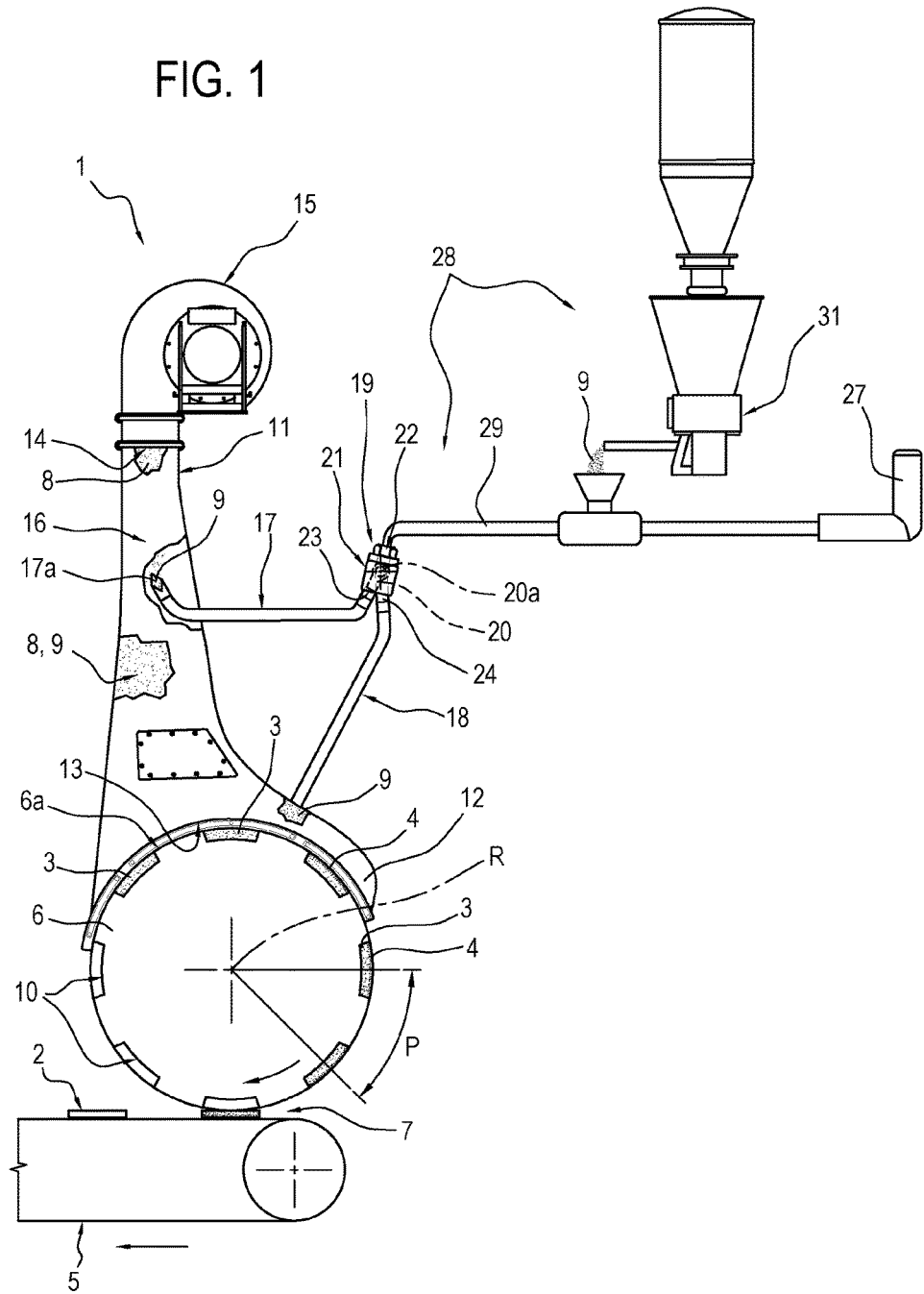
FIG. 1 is a schematic front view of a unit for making absorbent pads for absorbent articles according to this invention and according to a first embodiment of it.

With reference to FIG. 1, the numeral 1 denotes in its entirety a unit for making absorbent pads 2 of absorbent articles.

In general, the absorbent articles comprises a sheet of permeable material and a sheet of impermeable material having, sandwiched between them, an absorbent pad 2 constituting the part of the article whose function is to absorb liquids. For this purpose, the absorbent pad 2 is made mostly of natural fibre material (fluff) 8 blended with absorbent polymer material ("SAP") 9.

Generally speaking, each absorbent pad 2 comprises at least a first absorbent material 8, usually a natural fibre material, in particular fluff, and a second absorbent material 9, usually a superabsorbent polymer material, in particular SAP, different from the first absorbent material 8.

The natural fibre material 8, mixed with the absorbent polymer material 9, forms an absorbent matrix 3 of the pad 2.

Preferably, the absorbent polymer material 9 is a superabsorbent polymer material in granular form.

To increase its absorbent capacity, the pad 2 comprises at least one discrete layer 4 made mainly from absorbent polymer material 9.

The unit 1 comprises a feed line 5 along which the absorbent pads 2 feed once they are formed.

The unit 1 comprises a drum 6 for forming the pads 2.

The drum 6 is substantially tangent to the line 5 at a release station 7.

The drum 6 rotates about a relative horizontal axis of rotation perpendicular to the feed line 5.

As illustrated in FIG. 1, the drum 6 rotates about its axis R in a clockwise direction.

The drum 6 has a peripheral cylindrical surface 6a with at least one suction recess 10 formed thereon.

In the embodiment illustrated, the peripheral surface 6a has a plurality of suction recesses 10 angularly distributed along its surface of revolution.

The suction recesses 10 are located on the peripheral surface 6a of the drum 6 at a predetermined spacing P.

The unit 1 comprises a hood 11 for feeding at least the first and the second absorbent materials 8, 9 to at least part of the peripheral surface 6a of the drum 6.

In the preferred embodiment, the hood 11 is located above the drum 6.

In other words, the drum 6 is interposed between the feed line 5 and the feeding hood 11.

Together with the drum 6, the hood 11 defines a closed chamber for forming the pads 2 inside the recesses 10.

In the preferred embodiment, the hood 11 comprises a protrusion 12 defining a lateral extension of the hood 11.

More specifically, the lateral protrusion 12 extends along the peripheral surface 6a of the drum 6.

The protrusion 12 has an elongate shape and extends in a substantially circumferential direction.

In a variant not illustrated, the hood 11 comprises two protrusions 12 or lateral extensions.

In a further variant not illustrated, the hood 11 does not have any protrusion 12.

The hood 11 has an opening 13 for dispensing the first and the second absorbent materials 8, 9 facing each other to at least part of the peripheral surface 6a of the drum 6.

The hood 11 has an inlet opening 14 located at one of the ends of the hood 11, on the side opposite the dispensing opening 13.

The cross-sectional structure of the hood 11 is divergent in shape from the inlet opening 14 to the dispensing opening 13.

The hood 11 comprises a blower 15, located at the inlet opening 14, for supplying the natural fibre material 8 under pressure.

The hood 11 has a chamber 16 for mixing the first and the second absorbent materials 8, 9.

The mixing chamber 16 is positioned downstream of the inlet opening 14.

The mixing chamber 16 defines a zone of the hood 11 for mixing and transporting the natural fibre material 8 and the absorbent material 9.

The dispensing opening 13 feeds the first and second absorbent materials 8, 9 in the recesses 10 of the drum 6 filling them gradually for as long as they are positioned, following rotation of the drum 6, facing the hood 11.

With reference to the direction of rotation of the drum 6, once the peripheral surface 6a of the drum 6 facing the hood 11 moves out of the zone of action of the dispensing opening 13, the suction recesses 10 house respective finished absorbent pads 2 which are released by the drum 6 to the feed line 5 at the release station 7.

It should be noted that since the drum 6 overturns the absorbent pads 2 along the feed line 5, the position of the discrete absorbent layers in the absorbent pad 2 advancing along the feed line 5 is upside down relative to their position inside the recesses 10 of the drum 6.

The unit 1 comprises at least a first and a second duct 17 and 18 for feeding the second absorbent material 9 into the hood 11.

The first duct 17 leads into the mixing chamber 16 of the hood 11 and the second feed duct 18 leads close to the dispensing opening 13 of the hood 11.

The first duct 17 has an outlet opening 17a for the second absorbent material 9 in communication with the mixing chamber 16 of the hood 11.

In the preferred embodiment, the second duct 18 leads to the protrusion 12.

The second duct 18 makes the above-mentioned discrete layers 4 of absorbent material 9.

In the embodiment illustrated, the discrete layers 4 are made above at least part of the absorbent matrix 3 of the pad 2 positioned in the respective recess 10.

Advantageously, the unit 1 comprises distribution means 19 for feeding both the first and the second feed duct 17, 18.

The distribution means 19 feed alternately the first duct 17 and the second duct 18 and vice versa.

The first and second ducts 17, 18 are both connected to the distribution means 19.

Advantageously, the distribution means 19 feed the second absorbent material 9 into the second duct 18 as a function of the spacing P of the forming recesses 10 for making the discrete layers 4.

This guarantees the placing of the second absorbent material 9 at a respective recess 10, preventing placing along the peripheral surface 6a of the drum 6 between two consecutive recesses 10.

The distribution means 19 comprise a diverter 20 rotatable about a respective axis of rotation 20a.

The diverter 20 rotates about its own axis of rotation 20a to pass from a first feed position of the first duct 17 to a second feed position of the second duct 18, and vice versa.

It should be noted that the first feed position of the first duct 17 corresponds to the feed shut off, or closed, position of the second duct 18 and the second feed position of the second duct 18 corresponds to the feed shut off, or closed, position of the first duct 17.

In a first variant embodiment not illustrated, the diverter 20 rotates continuously about its own axis of rotation 20a and in a single predetermined direction of rotation to pass from the first feed position of the first duct 17 to the second feed position of the second duct 18, and vice versa.

Figure 2:
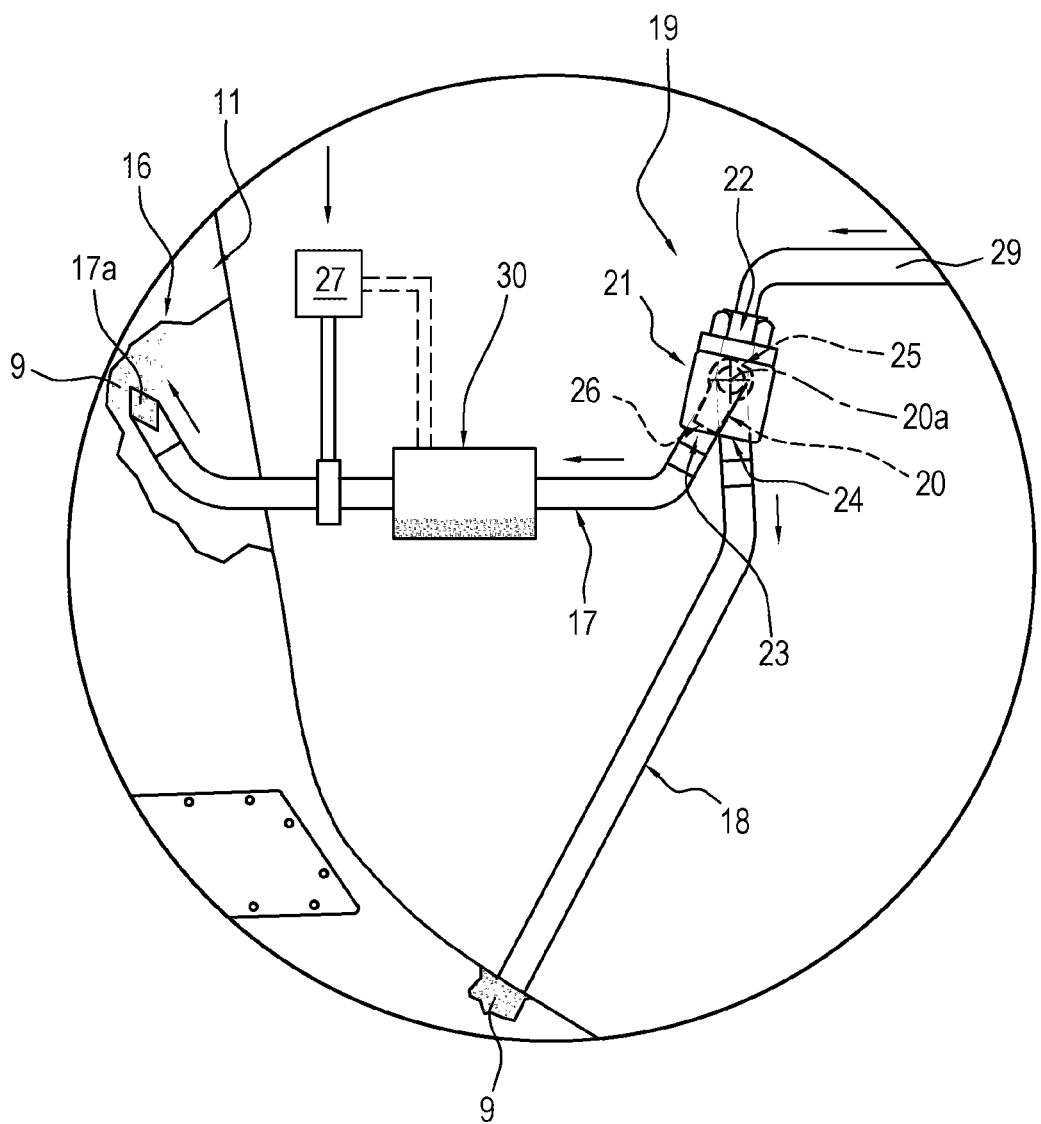
FIG. 2 is a scaled-up schematic front view of a detail of the unit of FIG. 1 according to a second embodiment.

According to a second embodiment illustrated in FIG. 2, the diverter oscillates about its own axis of rotation 20a to pass from the first feed position of the first duct 17 to the second feed position of the second duct 18, and vice versa.

Preferably, the diverter 20 is defined by a pipe union.

The pipe union 20 has an inlet mouth 25 and an outlet mouth 26.

The axis of rotation 20a of the diverter 20 is oriented along a direction parallel to the axis of rotation R of the forming drum 6.

The axis of rotation 20a of the diverter 20 is a horizontal axis.

The distribution means 19 comprise a body 21 for housing the diverter 20.

The housing body 21 has an infeed section 22 for introduction of the second absorbent material 9 and a first and a second outfeed section 23, 24, each of which is in communication, respectively, with the first and second feed ducts 17, 18.

With reference to the pipe union 20, the inlet section 22 of the housing body 21 communicates with the inlet mouth 25 of the pipe union 20.

The first and a second outfeed sections 23, 24 are alternately in communication with the outlet mouth 26 of the pipe union 20 during oscillation of the pipe union 20 around the relative axis of rotation 20a.

A pressurised air source 27 is connected to the distribution means 19.

More specifically, the air source 27 is connected to the body 21 for housing the diverter 20.

During the passage of the diverter 20 from the first to the second feed position of the first and the second ducts 17, 18, the air source 27 is alternately in fluid communication with the first and the second feed ducts 17, 18.

Advantageously, the unit 1 comprises a single plant 28 for feeding the second absorbent material 9, saving considerably on the management and maintenance costs of the unit 1.

The plant 28 comprises at least one infeed duct 29 for the second absorbent material 9 connected to the distribution means 19, in particular to the body 21 housing the diverter 20.

In practice, the distribution means 19 operate between the infeed duct 29 and the first and second feed ducts 17, 18 for feeding the second absorbent material 9 to the first duct 17 or to the second duct 18 from the duct 29. In other words, the ducts 17 and 18 are in communication with the infeed duct 29 by way of the distribution means 19 and are fed, preferably alternately, by the same distribution means 19.

Generally speaking, the distribution means 19 of the second absorbent material 9 are in common with the first feed duct 17 and with the second feed duct 18, which are therefore both connected to, and in communication with, the distribution means 19.

In general terms, the plant 28 defines a source for feeding the second absorbent material 9 to the distribution means 19.

Preferably, the air source 27 is in communication with the infeed duct 29.

The plant 28 comprises at least one doser unit 31 in communication with the infeed duct 29 for feeding predefined quantities of the second absorbent material 9, preferably in a continuous manner.

For example, the doser unit 31 may be defined by a screw feeder for distributing the second absorbent material 9.

It should be noted that in the embodiment illustrated, the second absorbent material 9 is defined by a single type of SAP.

In alternative embodiments not illustrated, the plant 28 comprises a plurality of doser units 31, each relating to a different type of SAP.

Advantageously, the first duct 17 feeds doses of absorbent polymer material 9 proportional to the quantity of natural fibre material 8.

With reference to FIG. 2, the first duct 17 comprises means 30 for accumulating the second absorbent material 9 positioned downstream of the diverter 20.

The accumulator means 30 are interposed between the first outfeed section 23 of the housing body 21 and the outfeed opening of the first duct 17 in communication with the mixing chamber 16.

In order to introduce the second absorbent material 9 placed in the accumulator means 30, a source 27 of air under pressure is connected to the accumulator means 30 or to the stretch of the first duct 17 downstream of the accumulator means 30.

The second embodiment of the unit 1 differs from the first embodiment in that the accumulator means 30 allow continuous feeding of the second absorbent material 9 into the mixing chamber 16 using the first duct 17, independently of the distribution of the diverter 20.

Advantageously, the first duct 17 continuously feeds the second absorbent material 9 into the mixing chamber 16 guaranteeing a good degree of mixing between the first and the second absorbent material 8, 9, whilst the second duct 18 continues to feed the second absorbent material 9 intermittently in order to make the above mentioned discrete layers 4.

In effect, in the first embodiment, the first duct 17 feeds the mixing chamber 16 intermittently as a function of the distribution of the diverter 20.

Advantageously, the use of distribution means 19 common to the first and the second duct 17, 18 make it possible to prevent recirculation of the second absorbent material 9, preserving as much as possible the integrity of the second absorbent material 9.

This invention also relates to a method for making absorbent pads of absorbent articles which comprises a step of feeding the first and the second absorbent materials 8, 9 and mixing the first and the second absorbent materials 8, 9 in the hood 11.

More specifically, the feeding step comprises feeding the second absorbent material 9 using at least a first and a second feed duct 17, 18 leading into the hood 11

According to this invention, the method comprises a step of distributing the second absorbent material 9 into the first and second feed ducts 17, 18 from the same feed source 2.

The step of feeding the second absorbent material 9 is performed in continuous manner.

The step of distributing the second absorbent material 9 is performed in an alternating manner between the first and the second feed duct 17, 18, and vice versa.

The invention claimed is:

1. A unit for making absorbent pads of absorbent articles, each absorbent pad comprising a first absorbent material including a natural fiber material, and a second absorbent material different from the first absorbent material, the second absorbent material including a superabsorbent polymer material; the unit comprising:
   a forming drum including a peripheral surface,
   a hood for feeding the first and the second absorbent materials to at least part of the peripheral surface of the forming drum;
   the hood including a mixing chamber for mixing the first and the second absorbent materials and an opening for dispensing the first and the second absorbent materials, the opening facing at least part of the peripheral surface of the forming drum;
   a first feed duct and a second feed duct for feeding the second absorbent material into the hood;
   a distribution mechanism for distributing the second absorbent material in common with the first feed duct and the second feed duct; the first and the second feed ducts being connected to the distribution mechanism; the distribution mechanism including a body and a diverter supported by the body, the diverter being alternately connectable between a flow connection with the first feed duct and a flow connection with the second feed duct.

2. The unit according to claim 1, and further comprising a single plant for feeding the second absorbent material; the plant comprising at least one infeed duct of the second absorbent material in communication with the distribution mechanism.

3. The unit according to claim 1, wherein the distribution mechanism feeds the first and the second feed ducts intermittently.

4. The unit according to claim 1, wherein the first feed duct leads into the mixing chamber of the hood and the second feed duct leads to a position adjacent the dispensing opening of the hood.

5. The unit according to claim 1, wherein the peripheral surface includes a plurality of recesses for forming the absorbent pads arranged according to a predetermined spacing; the distribution mechanism feeding the second absorbent material into the second feed duct as a function of the spacing of the forming recesses.

6. The unit according to claim 1, wherein the diverter is rotatable about an axis of rotation; the diverter rotating about the axis of rotation to pass from a first feed position in the flow connection with the first feed duct to a second feed position in the flow connection with the second feed duct, and vice versa.

7. The unit according to claim 6, wherein the diverter rotates continuously about the axis of rotation and in a single predetermined direction of rotation to pass from the first feed position to the second feed position and from the second feed position to the first feed position.

8. The unit according to claim 6, wherein the diverter oscillates about the axis of rotation to pass from the first feed position to the second feed position, and vice versa.

9. The unit according to claim 6, and further comprising a source of pressurized air connected to the distribution mechanism; the source of pressurized air source being alternately in fluid communication with the first and the second feed ducts as a function of the first and the second feed positions.

10. The unit according to claim 1, wherein the first feed duct comprises an accumulator chamber for accumulating the second absorbent material located downstream of the diverter; the accumulator chamber continuously feeding the mixing chamber of the hood.

11. The unit according to claim 10, and further comprising a source of pressurized air connected to the accumulator chamber or to the stretch of the first feed duct downstream of the accumulator chamber.

12. A method for making absorbent pads of absorbent articles, each absorbent pad comprising a first absorbent material including a natural fiber material, and a second absorbent material different from the first absorbent material, the second absorbent material including a superabsorbent polymer material; the method comprising:
- feeding the first and the second absorbent materials to a hood;
- mixing the first and the second absorbent materials in the hood;
- wherein the feeding step comprises feeding the second absorbent material using both a first feed duct and a second feed duct leading into the hood;
- distributing the second absorbent material into the first and the second feed ducts from a same feed source;
- wherein the distributing the second absorbent material is performed in an alternating manner between the first and the second feed ducts, and vice versa.

13. The method according to claim 12, wherein the feeding the second absorbent material is performed in a continuous manner.

* * * * *